United States Patent
Sivavec et al.

(10) Patent No.: US 6,743,915 B2
(45) Date of Patent: Jun. 1, 2004

(54) POLY (1,4-ETHYLENE-2-PIPERAZONE) COMPOSITION, METHOD FOR PRODUCTION OF A POLY(1,4-ETHYLENE-2-PIPERAZONE), COMPOSITION TCE-DETECTING METHOD AND SENSOR

(75) Inventors: Timothy Mark Sivavec, Clifton Park, NY (US); Radislav Alexandrovich Potyrailo, Niskayuna, NY (US)

(73) Assignee: General Electric Company, Niskayuna, NY (US)

(\*) Notice: Subject to any disclaimer, the term of this patent is extended or adjusted under 35 U.S.C. 154(b) by 0 days.

(21) Appl. No.: 10/226,813

(22) Filed: Aug. 26, 2002

(65) Prior Publication Data

US 2003/0040121 A1 Feb. 27, 2003

Related U.S. Application Data

(62) Division of application No. 09/441,851, filed on Nov. 17, 1999, now Pat. No. 6,461,872.

(51) Int. Cl.$^7$ ............................................. C07D 241/08
(52) U.S. Cl. ....................................................... 544/384
(58) Field of Search ........................................ 544/384

(56) References Cited

U.S. PATENT DOCUMENTS

| | | | |
|---|---|---|---|
| 4,112,090 A | \* | 9/1978 | Saikawa et al. |
| 4,892,383 A | | 1/1990 | Klainer et al. |
| 4,929,562 A | | 5/1990 | Anderson, deceased et al. |
| 4,980,471 A | \* | 12/1990 | Christiansen et al. |
| 5,358,875 A | | 10/1994 | Goswami et al. |
| 5,525,520 A | | 6/1996 | Dinh |

FOREIGN PATENT DOCUMENTS

| | | |
|---|---|---|
| GB | 1054348 | 1/1967 |
| WO | 9301368 | 3/1993 |

OTHER PUBLICATIONS

Chemical Sensors and Microinstrumentation,"New Developments and Applications of Fiber–Optic Sensors", SM Angel, et al, 1989 American Chemical Society, Chapter 23, pp. 345–363.
Pergamon, "A Fiber–Optic Sensor System for Monitoring Chlorinated Hydrocarbon Pollutants", FP Milanovich, et al, Talunta, vol, 41, No. 12, pp. 2189–2194, 1994, Elsevier Science Ltd., Printed in Great Britain.
Journal of Cheomometrics, "A Second–Order Standard Addition Method With Application to Calibration of a Kinetics–Spectroscopic Sensor for Quantitation of Trichloroethylene", Karl Booksh, et al, 1995, vol. 9, pp 263–282.
Fiber Optic Sensors for Rapid, Inexpensive Characterization and Soil and Ground Water Contamination, Fred P. Milanovich, et al, Proceedings of Petroleum hydrocarbons and organic Chemicals in Ground Water: Prevention, Detection, & Remediation Conf., Nov. 2–4, 1994,.

Field Testing of a portable Trichlorethylene and chloroform Fiber Optic Chemical Sensor, James C. Wells, et al, Presented at the Tenth Annual Waste Testing and Quality Assurance Symposium, Arlington, Virginia, Jul. 11–15, 1994.
Preliminary Field Demonstration of a Fiber–Optic TCE Sensor, SM Angel, et al, SPIE vol. 1368 Chemical, Biochemical, and Environmental Fiber Sensor II, 1990, pp 98–104.
Tetrahedron, Trichlorethylene In Organic synthesis: II. Reaction of Trichlorethylene With Secondary Amines, Jan Pielichowski, et al, vol. 40, No. 14, pp 2671–2675, 1984.
Polish Journal of Chemistry, Application of Trichlorethylene in Organic Synthesis, part III\*, Synthesis of Dichloroviny Aromatic Ethers, 62, 1988, pp. 483–487, Pielichowski et al.

\* cited by examiner

*Primary Examiner*—Emily Bernhardt
(74) *Attorney, Agent, or Firm*—Kimberly Parker; Patrick K. Patnode

(57) ABSTRACT

A composition of matter has the formula:

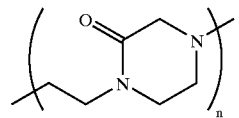

where n is an integer equal or greater than 1. The composition of matter possesses characteristic absorbance behavior with respect to infrared and visible energy, which is used to detect and determine the concentration of TCE. In another aspect, a method for generating the composition comprises reacting trichloroethylene (TCE) with poly(ethylenimine) in accordance with the formula:

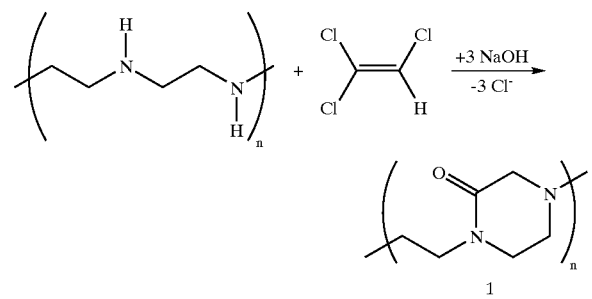

(1)

where n is an integer equal or greater than 1. Also, the invention sets forth a sensor to detect trichloroethylene (TCE) in materials. The sensor includes the composition of material that can absorb at least one of infrared (IR) or ultraviolet (UV) or visible (VIS) energies when formed by the reaction of trichloroethylene (TCE) with poly (ethylenimine).

2 Claims, 5 Drawing Sheets

POLY (1,4-ETHYLENE-2-PIPERAZONE) COMPOSITION, METHOD FOR PRODUCTION OF A POLY(1,4-ETHYLENE-2-PIPERAZONE), COMPOSITION TCE-DETECTING METHOD AND SENSOR

This application is a division of application Ser. No. 09/441,851, filed Nov. 17, 1999, now U.S. Pat. No. 6,561,782, which is hereby incorporated by reference in its entirety.

BACKGROUND OF THE INVENTION

The invention relates a poly(1, 4-ethylene-2-piperazone) composition, a method of production of the poly(1,4-ethylene-2-piperazone) composition, the use of the poly(1, 4-ethylene-2-piperazone) composition in the detection of trichloroethylene (TCE), and a sensor using the poly(1,4-ethylene-2-piperazone) composition.

Halogenated hydrocarbons, such as chlorinated hydrocarbons and chlorinated solvents (hereinafter collectively referred to as "chlorinated solvents") are commonly used in industry as chemical carriers, solvents, paint removers, and cleaners. The chlorinated solvents have low flammability and are fairly stable, both chemically and biologically. Chlorinated solvents are alsoused a's intermediates in chemical manufacturing and as carrier solvents for pesticides and herbicides.

Chlorinated solvents are relatively toxic at low levels, and many chlorinated solvents have been classified as suspected or confirmed carcinogens. Chlorinated solvents are prevalent contaminants in groundwater and soil because of their widespread use and long-term stability. Chlorinated solvents from various sources have contaminated groundwaters and soils. These sources include, but are not limited to, disposal facilities, chemical spills, and leaking underground storage tanks. Chlorinated solvents also may be released to the environment through the use, loss, or disposal of a neat liquid, and alternatively through the use or disposal of wash and rinse waters containing residual solvents. In recent years, soil and groundwater contamination by chlorinated solvents has become a recognized environmental problem. Chlorinated ethylenes, such as trichloroethylene (TCE), tetrachloroethylene (commonly known as perchloroethylene (PCE)), and chlorinated ethanes, such as 1,1,1,-trichloroethane (TCA), are recognized as environmental pollutants. Due to the high water solubility of chlorinated solvents, for example about 1100 mg/l trichloroethylene (TCE) at about 25° C., chlorinated solvents are highly mobile in soils and aquifers, and thus, should be removed before dispersing too far in the soils and aquifers. Therefore, a method to detect chlorinated solvents in contaminated soil and groundwater is needed.

Sensors have been proposed to detect trichloroethylene (TCE), in which the sensors attempt to detect trichloroethylene (TCE) by a variety of methods, including reacting pyridine, trichloroethylene (TCE), a base, and appropriate phase-transfer catalysts to generate a trichloroethylene (TCE) indicator. Other proposed sensors rely on fiber optic chemical sensors, immuno-assay methods, and gas chromatography to measure amounts of trichloroethylene (TCE). The prior sensors are costly, are typically labor intensive, and may not provide real-time detection that can be analyzed and reported. While such proposed sensors may have limited applications, attempts to automate such sensors have not been successful.

Hand-held sensing units using the above-mentioned technology have been proposed, however, automating such sensors presents problems in incorporating reagent delivery systems. These hand-held units are often difficult to use, provide inaccurate reagent delivery, and present difficulties in field operations. Another problem associated with automation of the above-mentioned technology arises in the storage and disposal of the chemicals in the field.

Various materials and compositions have been proposed to detect the presence of trichloroethylene (TCE), and other materials and compositions. For example, litmus paper has been used to detect the presence of acidic or base compositions. While materials and compositions that detect other materials and compositions (hereinafter referred to as "detector compositions") are known, their applications in sensors are limited, more detector compositions for detecting chlorinated solvents are needed.

Therefore, a need exists for a composition to detect chlorinated solvents, such as trichloroethylene (TCE). Also, a need exists for a method to detect chlorinated solvents, along with a sensor that incorporates a composition to detect trichloroethylene (TCE), and avoids the above-mentioned problems.

SUMMARY OF THE INVENTION

Accordingly, the invention provides a composition of matter, in which the composition of matter is provided that has the formula:

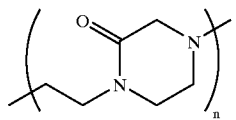

where n is an integer equal or greater than 1.

In another aspect, a method for generating the composition

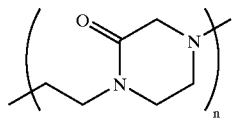

comprises reacting trichloroethylene (TCE) with poly (ethylenimine) in accordance with the Equation:

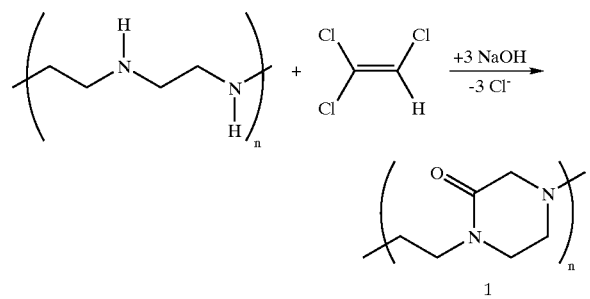

where n is an integer equal or greater than 1.

Also, the invention sets forth a sensor to detect trichloroethylene (TCE) in materials. The sensor includes the composition:

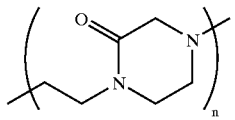

that can absorb at least one of infrared (IR) and visible (VIS) energy when formed by the reaction trichloroethylene (TCE) with poly(ethylenimine).

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

A poly(1,4-ethylene-2-piperazone) composition, as embodied by the invention, is designated by the following nomenclature:

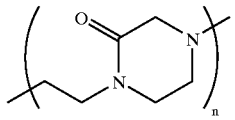

where n is an integer equal to or greater than 1.

Repeating units of the poly(1,4-ethylene-2-piperazone) composition, as embodied by the invention, can be formed by incorporating trichloroethylene (TCE) in repeating units of poly(ethylenimine) (PEI) in the presence of sodium hydroxide (NaOH) to generate repeating units of poly(1,4-ethylene-2-piperazone) (and sodium chloride (NaCl) as a by-product), in accordance with Equation (1):

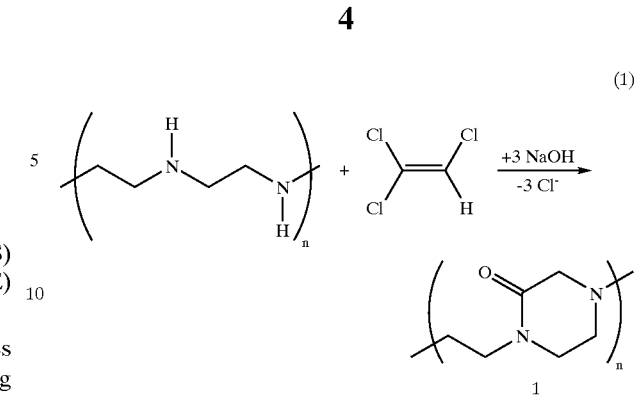

where n is an integer equal to or greater than 1.

Alternatively, a single unit of the poly(1,4-ethylene-2-piperazone) composition, as embodied by the invention, can be formed by incorporating trichloroethylene (TCE) in N,N'-dialkylethylenediamine 2 in the presence of sodium hydroxide (NaOH) and chlorine (Cl$^-$) to generate N,N'-dialkyl-2-piperazone 3 (and sodium chloride (NaCl) as a by-product), in accordance with Equation (2):

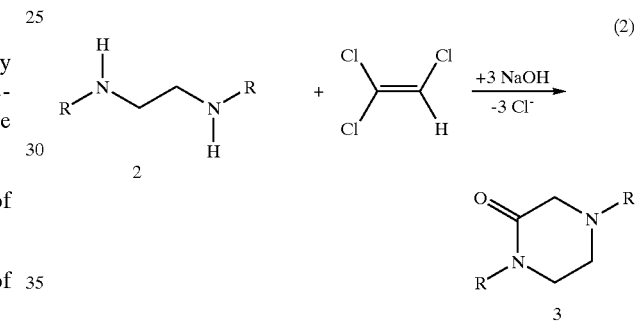

The poly(1,4-ethylene-2-piperazone) and N,N'-dialkyl-2piperazone (compound formula 3) as embodied by the invention, that is produced in accordance with either Equations (1) and (2) above, exhibits an enhanced infrared (IR) absorbance of infrared wavelength energy. The enhanced infrared absorbance for the poly(1,4-ethylene-2-piperazone) is especially evident at infrared frequencies at about 1658 cm$^{-1}$. An amount of trichloroethylene (TCE) can be determined from the intensity the infrared (IR) absorbance at 1658 cm$^{-1}$ in poly(1,4-ethylene-2-piperazone), which is related to trichloroethylene (TCE) concentrations in the material. Therefore, the poly(1,4-ethylene-2-piperazone), as embodied by the invention, that is formed by the incorporation of trichloroethylene (TCE) into poly(ethylenimine) (PEI), can act as a sensing composition for trichloroethylene (TCE) as monitored by its infrared (IR) absorbance.

Figure 1:
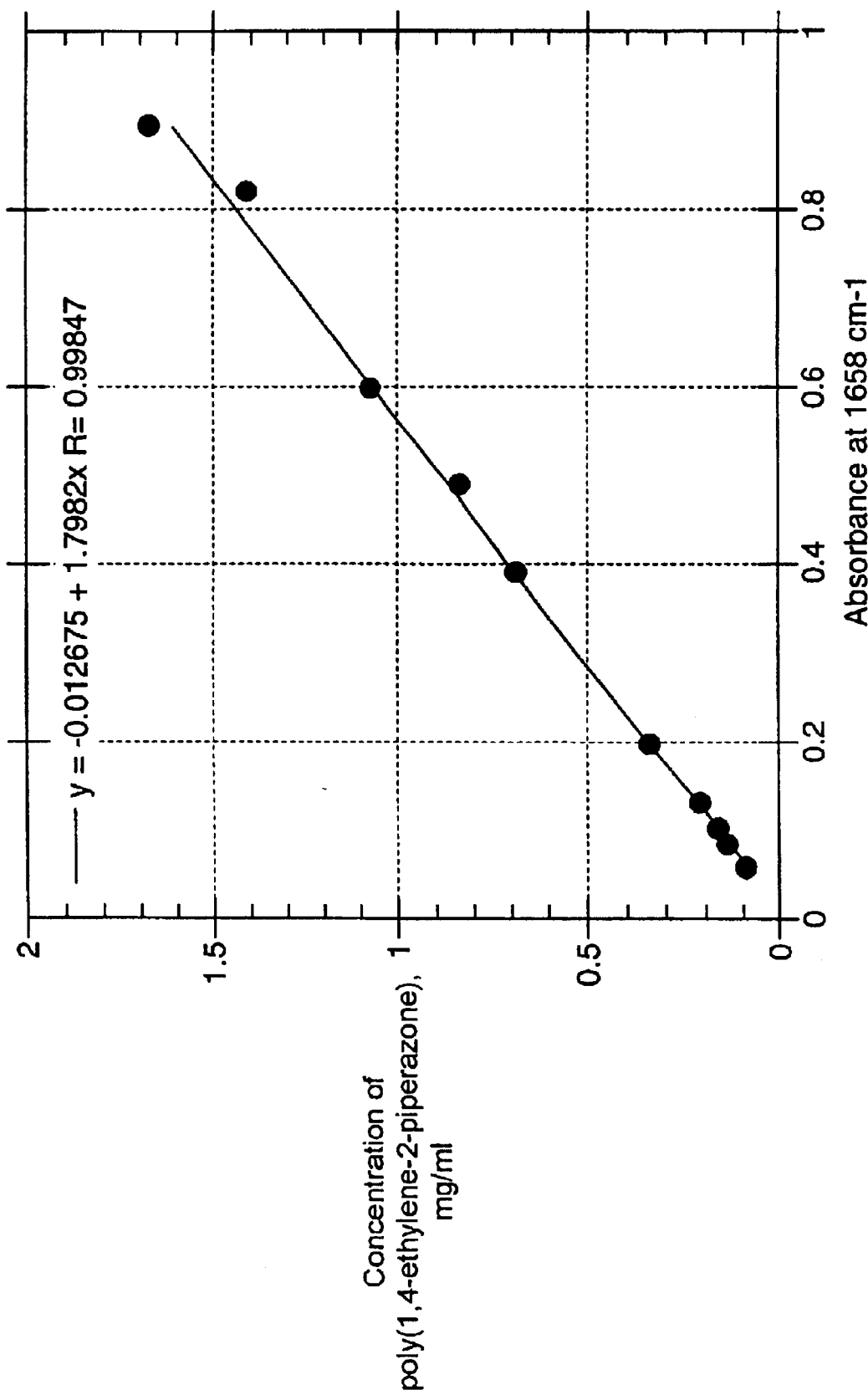
FIG. 1 is a graph of concentration versus absorbance at 1658 cm$^{-1}$ for poly(1,4-ethylene-2-piperazone), as embodied by the invention.

FIG. 1 is an exemplary graph of concentration versus absorbance at 1658 cm-1 for poly(1,4-ethylene-2-piperazone). Amounts of trichloroethylene (TCE) in a soil or groundwater samples or in the soils or groundwaters themselves may be readily determined from such a graph by recognizing its relationship with poly(1,4-ethylene-2-piperazone), for example given by Equations (2) or (3).

Figure 2:
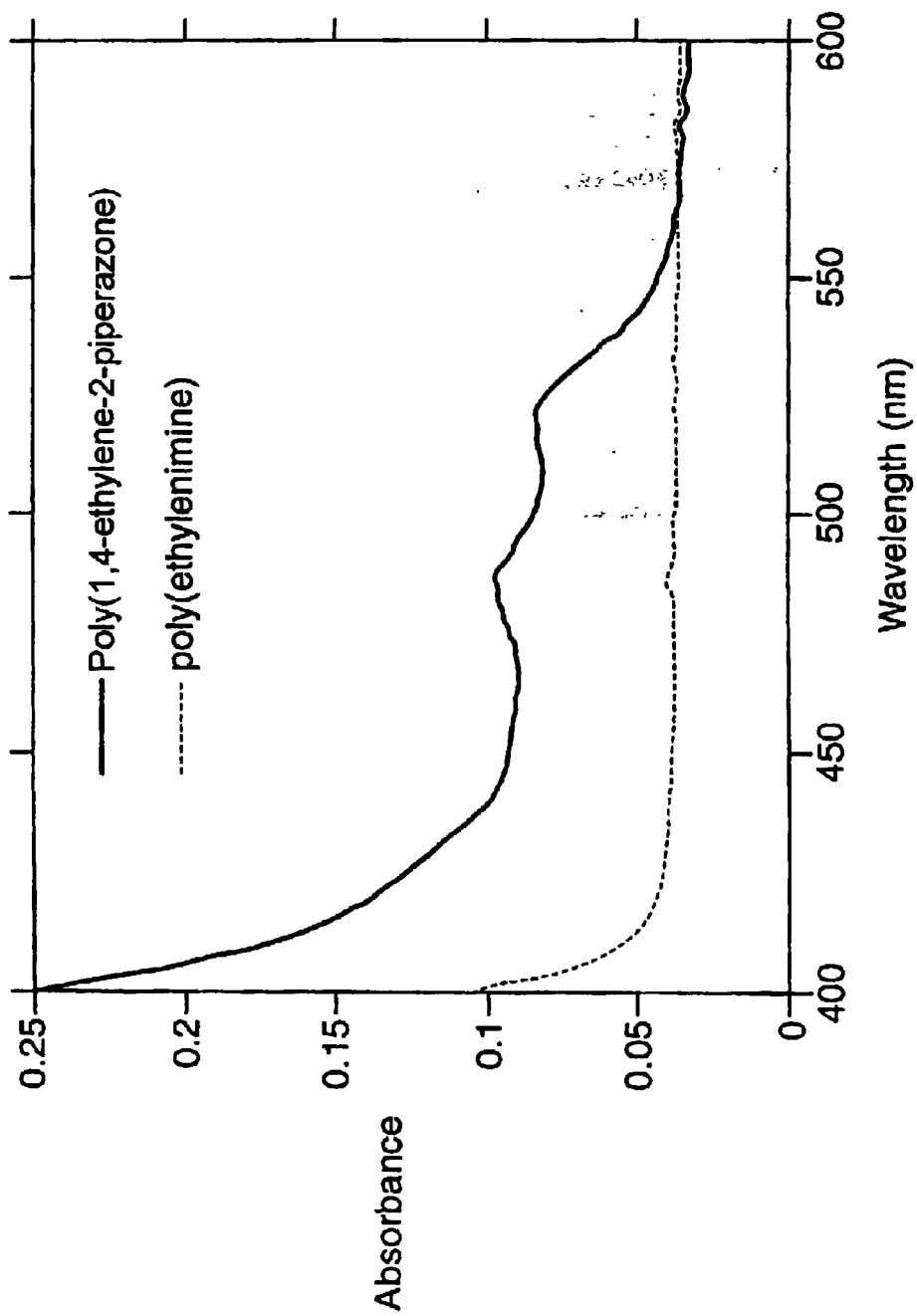
FIG. 2 is a graph of visible (VIS) spectrum of poly (ethylenimine) compared to poly(1,4-ethylene-2-piperazone) generated in a reaction, as embodied by the invention.

The poly(1,4-ethylene-2-piperazone) and N,N'-dialkyl-2-piperazone 3 that are produced in accordance with Equations (1) and (2) exhibit characteristic absorbance of visible (VIS) energy in the spectral region from about 400 nm to about 525 nm as illustrated in FIG. 2. This characteristic absorbance may be used to detect and determine trichloroethylene (TCE) concentrations that have reacted with poly (ethylenimine) (PEI), as in Equation (1).

The poly(1,4-ethylene-2-piperazone), as embodied by the invention, may be incorporated in a sensor for detecting trichloroethylene (TCE). The detection of the trichloroethylene (TCE) may be for trichloroethylene (TCE) in at least one of groundwaters, flowing waters such as rivers, standing waters such as lakes, and other water containing materials. The detection of the trichloroethylene (TCE) may also be applied to unsaturated soils or vadose zones. A sensor that incorporates poly(1,4-ethylene-2-piperazone), as embodied by the invention, can monitor relatively low concentrations, for example as low as about 5 $\mu$g/l, of chlorinated hydrocarbons, such as trichloroethylene (TCE).

A sensor as embodied by the invention, for detecting chlorinated solvents may be provided in a test kit, hand-held field test unit, or other self-contained sensing unit (hereinafter "test kit") for field use in monitoring contaminants. The test kit may comprise a unit that a user carries to various testing sites. Alternatively, the test kit may comprise a unit that is left at a testing site and provides contaminant data, for example, by remote monitoring to a control or service center.

Exemplary sensors, sensor probes, and other components that utilize the poly(1,4-ethylene-2-piperazone), as embodied by the invention, are illustrated in FIGS. 3–6.

Figure 3:
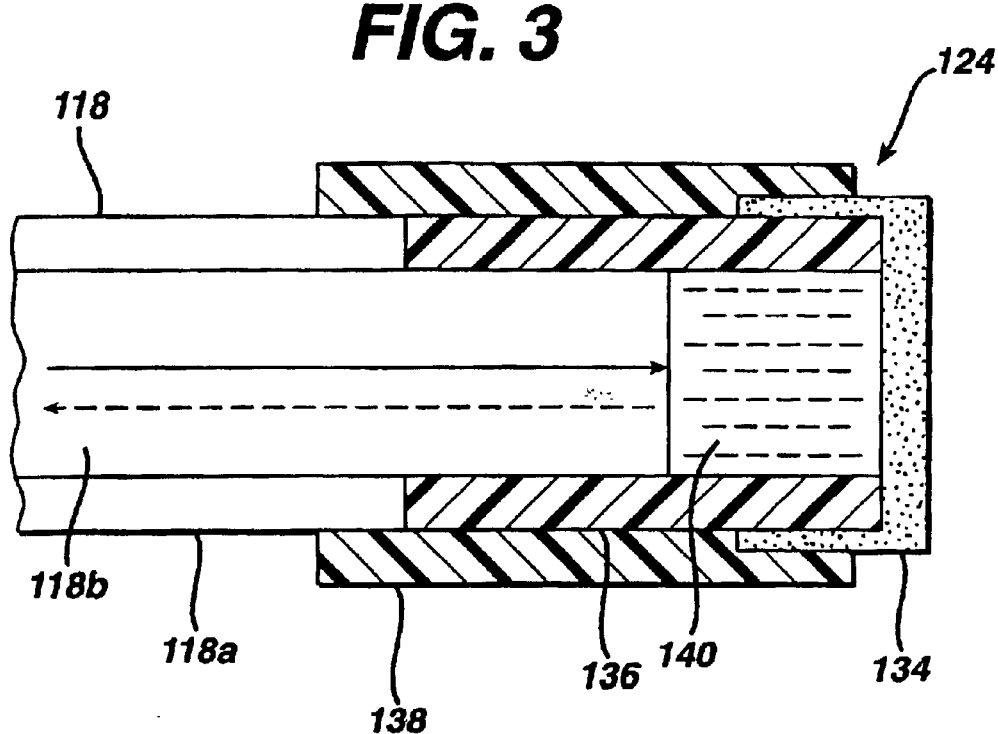
FIG. 3 is an enlarged, longitudinal sectional illustration of a sensor probe, as embodied by the invention.

FIG. 3 is a schematic illustration of a photo-activated luminescence sensor 124. The sensor 124 can comprise a bifurcated fiber optic system having first and second optical fibers. The first fiber carries excitation energy from an energy source to a sensor probe, while the second fiber transmits the absorbance from the sensor probe to a photo detector. Dispersive devices and can be associated with the light source and the photo detector, respectively.

In FIG. 3, the sensor 124 comprises a single-fiber 118. The optical fiber 118 may be a plastic-clad fused-silica fiber, which includes an outer cladding 118a and an inner fiber core 118b. A membrane 134 can be stretched across the face of a length of plastic heat-shrink cylinder 136. Alternatively, the membrane 134 may be sealed on the cylinder 136. The membrane 134 may comprise a porous TEFLONTM or a suitable dialysis membrane material.

The cylinder 136 is tightly disposed on the fiber core 118b. When in place, a tight seal can be formed between the fiber core 118b and the plastic cylinder 136. A second heat shrink cylinder 138 can be over an end portion of the cladding 118a and the membrane 134 to ensure tightness and structural integrity of the sensor probe 124. A sensor probe cavity 140 is defined as a space between the end of the core 118b, the membrane 134, and the cylindrical sidewall of the cylinder 136. The size of the sensor probe cavity 140 is determined by the diameter of the fiber optic diameter and the heat-shrink cylinder 136.

Figure 4:
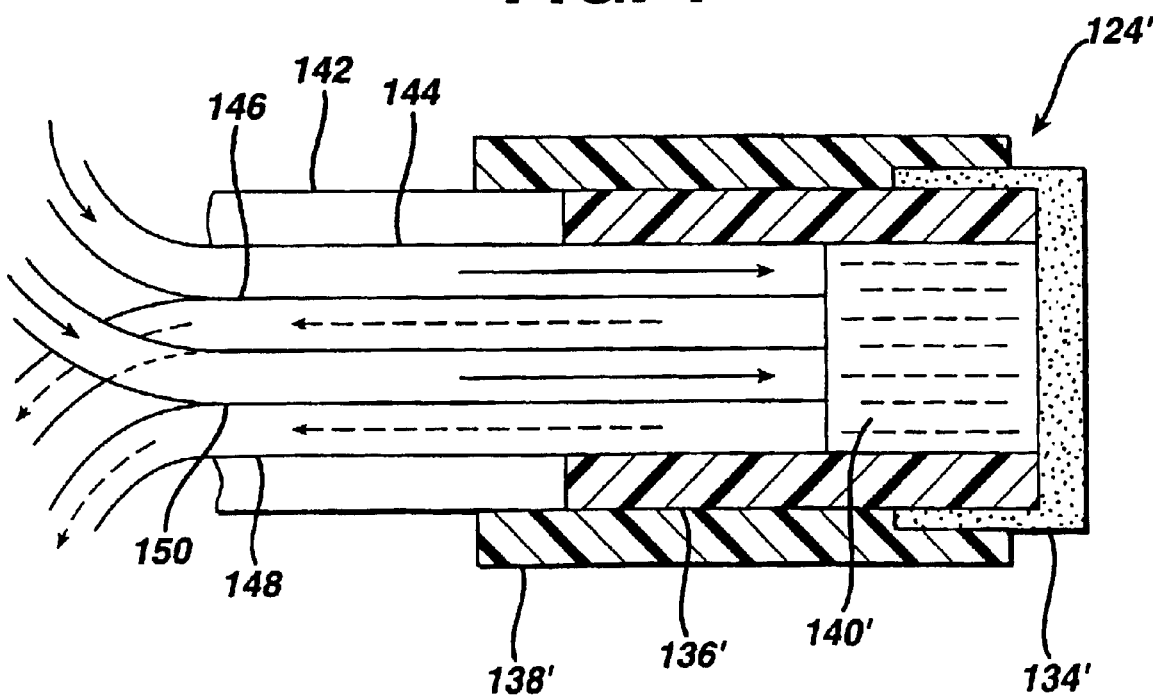
FIG. 4 is an enlarged, longitudinal sectional illustration of another sensor probe, as embodied by the invention.

A sensor probe of similar design for a bifurcated optical system is illustrated in FIG. 4, wherein the same, but primed, reference numerals are used to refer to like parts. In the bifurcated configuration, a common cladding 142 encases multiple fiber cores 144, 146, 148, and 150. Energy is illustrated with solid line directional arrows, while the absorption is illustrated with broken-line directional arrows.

The fiber core may comprise a single core, and alternatively the fiber core can comprise a bundle of fibers. For example, the plastic heat-shrink cylinder can be tapered, resulting in an inner diameter that contains the poly(1,4-ethylene-2-piperazone) producing material. The distance between the membrane and the fiber face can be adjusted, varying an approximate volume for the microcavity 140 on 140'. Alternatively, a poly(1,4-ethylene-2-piperazone) producing material may be embedded in a gel or sol-gel system or bound to solid particles, such as microbeads contained in the ricrocavity.

When the sensor probe 124 or 124' is placed in a trichloroethylene (TCE)-containing solution, trichloroethylene (TCE) readily passes through the membrane 134 or 134', diffuses into the microcavity 140 or 140', and interacts with the poly(1,4-ethylene-2-piperazone) producing material. Alternatively, the poly(1,4-ethylene-2-piperazone) producing material may be covalently bound to the fiber optic, such as the end of at each core 118b, 148, and 150. Thus, when infrared (IR) energy is directed to the poly(1,4-ethylene-2-piperazone) producing material an infrared (IR) absorbance that corresponds to the absorbance as in the graph of FIG. 1, can be produced.

Figure 5:
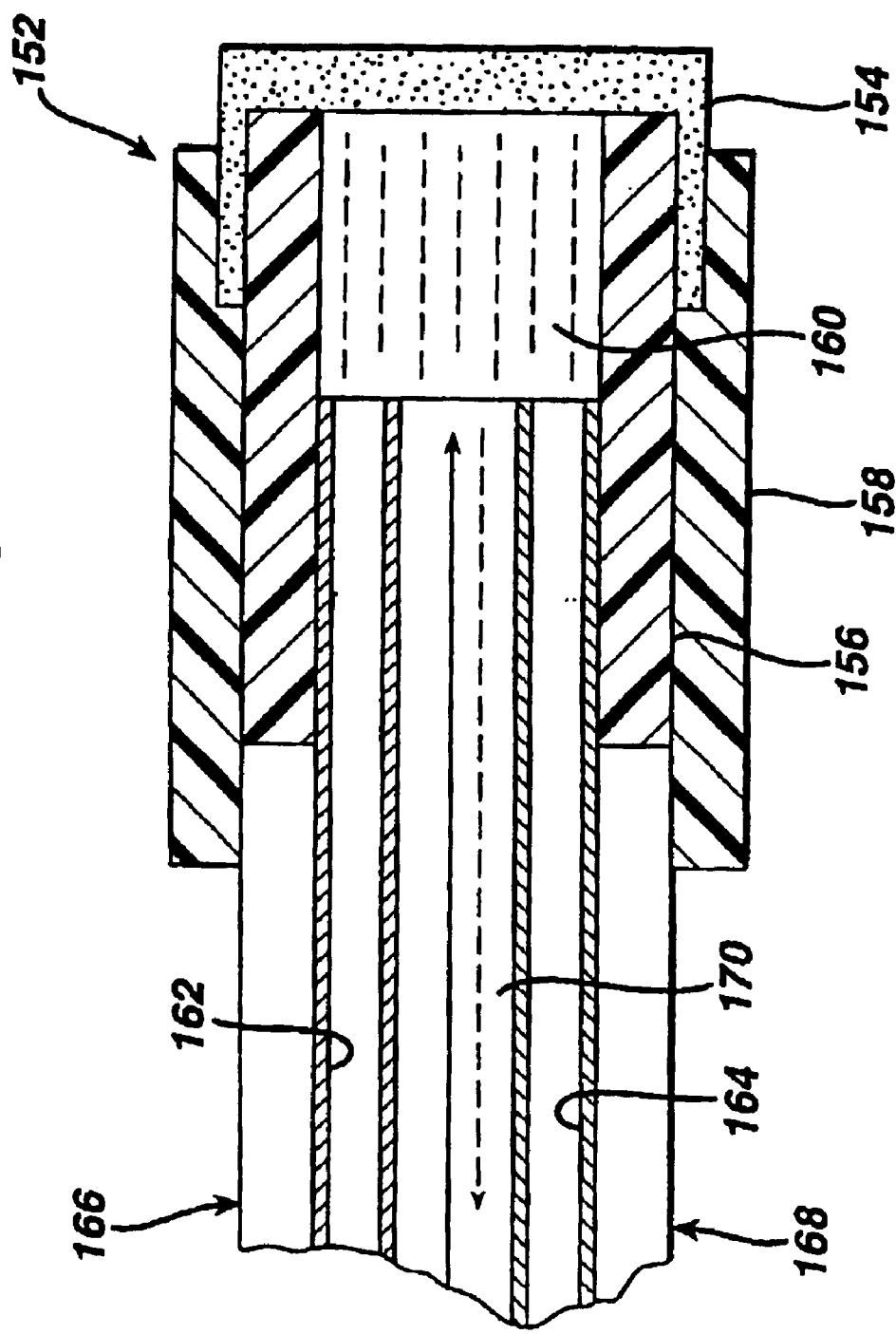
FIG. 5 is an enlarged longitudinal sectional illustration of another sensor probe, as embodied by the invention.

An alternative sensor probe, as embodied by the invention, is illustrated in FIG. 5. The sensor probe 152 comprises a porous membrane 154, first and second plastic cylinders 156 and 158, and a chamber 160, which may contain a quantity of poly(1,4-ethylene-2-piperazone) producing material. The poly(1,4-ethylene-2-piperazone) producing material can be introduced prior to testing, and then removed along with after testing, using one or more conduits 162 and 164. These conduits 162 or 164 are in fluid communication with the chamber 160. A single fiber 166 can be used with a single cladding 168 and single core 170, through which the excitation and emission radiation pass. The sensor probe of FIG. 5 allows regeneration of the sensing system after each measurement, if desired, so that multiple uses of this sensor probe are possible. The sensor probe of FIG. 5 allows rapid repetitive measurement of trichloroethylene (TCE).

Figure 6:
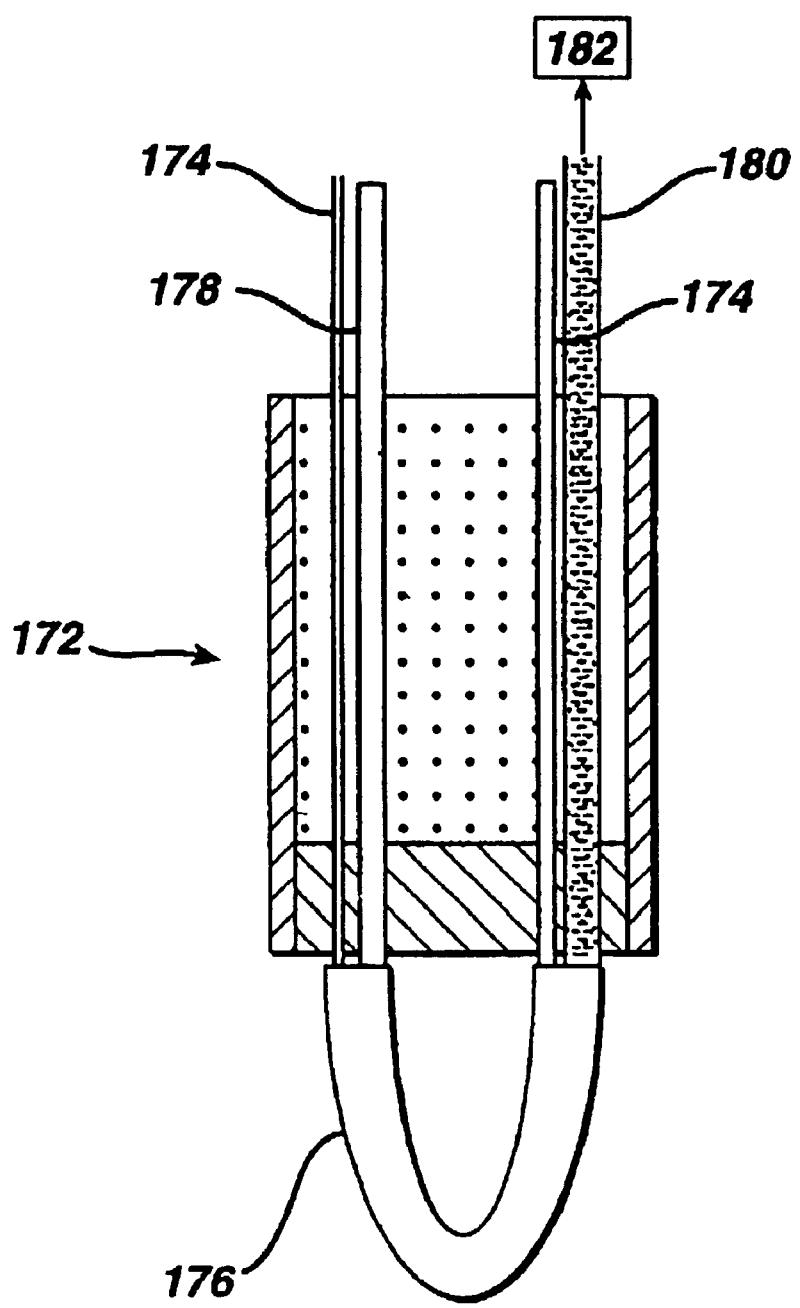
FIG. 6 is a yet another enlarged longitudinal sectional illustration of another sensor probe, as embodied by the invention.

A further sensor probe, as embodied by the invention, is illustrated in FIG. 6. The sensor probe 172 can comprise an optical fiber 174, which is led into a chamber body 176. The chamber body 176 defines a chamber that may include a quantity of poly(1,4-ethylene-2-piperazone) producing material. An air inlet conduit 178 extends into the poly(1,4-ethylene-2-piperazone) producing material and an air outlet conduit 180 is spaced therefrom. A pump 182 may be connected to the outlet 180 so as to cause air to circulate through the chamber body 176.

The poly(1,4-ethylene-2-piperazone) composition, its use in the sensors, and the sensing process described above has advantageous features. It is a relatively simple sensing process that combines absorption processes to yield measurements of trichloroethylene (TCE). The sensor probe facilitates the sensing volatile compounds that might otherwise be difficult to sense. Also, the methodology allows a quantitative determination of trichloroethylene (TCE) content, and provides rapid analysis and a capability of making in-situ or remote hands-free measurements.

While various embodiments are described herein, it will be appreciated from the specification that various combina-

What is claimed is:
1. A composition of matter having a formula of:
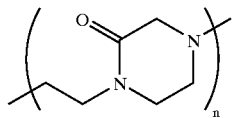
where n is an integer greater than 1.
2. A method of generating the composition of claim 1, the method comprising reacting trichloroethylene (TCE) with poly(ethylenimine) in accordance with the Equation:
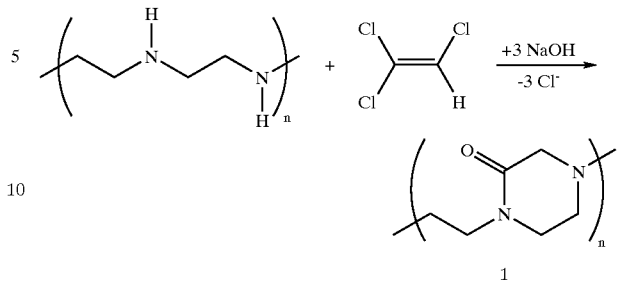
(1)
wherein n is greater than 1.
* * * * *